(12) United States Patent
Berlin et al.

(10) Patent No.: US 7,670,777 B2
(45) Date of Patent: Mar. 2, 2010

(54) METHOD FOR DETECTING DNA METHYLATION USING LABELLED S-ADENOSYLMETHIONINE ANALOGS

(75) Inventors: Kurt Berlin, Stahnsdorf (DE); Achim Ribbe, Duesseldorf (DE)

(73) Assignees: Epigenomics AG, Berlin (DE); Qiagen GmbH, Hilden (DE)

( * ) Notice: Subject to any disclaimer, the term of this patent is extended or adjusted under 35 U.S.C. 154(b) by 0 days.

(21) Appl. No.: 11/904,320

(22) Filed: Sep. 26, 2007

(65) Prior Publication Data
US 2008/0206760 A1 Aug. 28, 2008

Related U.S. Application Data

(63) Continuation of application No. 10/491,847, filed as application No. PCT/DE02/03844 on Oct. 4, 2002, now abandoned.

(30) Foreign Application Priority Data

Oct. 5, 2001 (DE) .................... 101 51 069

(51) Int. Cl.
C12Q 1/68 (2006.01)
(52) U.S. Cl. .......................................... 435/6
(58) Field of Classification Search .......... None
See application file for complete search history.

(56) References Cited

U.S. PATENT DOCUMENTS

| | | | |
|---|---|---|---|
| 5,567,596 A * | 10/1996 | Diamond et al. | 435/13 |
| 5,786,146 A * | 7/1998 | Herman et al. | 435/6 |
| 6,150,112 A * | 11/2000 | Weissman et al. | 435/6 |
| 6,251,639 B1 | 6/2001 | Kurn | |
| 7,179,594 B1 | 2/2007 | Berlin | |
| 2003/0032026 A1 | 2/2003 | Berlin | |
| 2004/0072197 A1* | 4/2004 | Jones et al. | 435/6 |

FOREIGN PATENT DOCUMENTS

| | | |
|---|---|---|
| DE | 199 35 772 A1 | 2/2001 |
| DE | 199 51 189 A1 | 5/2001 |
| WO | WO 92/06985 A1 | 4/1992 |
| WO | WO 99/10540 A1 | 3/1999 |
| WO | WO 01/27317 A2 | 4/2001 |
| WO | WO 02/101353 A2 | 12/2002 |

OTHER PUBLICATIONS

Mass et al. ("Arsenic alters cytosine methylation patterns of the promoter of the tumor suppressor gene p53 in human lung cells: a model for a mechanism of carcinogenesis" Mutat Res. Jun. 1997;386(3):263-77).*
Markoulatos et al. ("Multiplex polymerase chain reaction: a practical approach" J Clin Lab Anal. 2002;16(1):47-51).*
Rampersaud et al., "Genomic DNA methylation decreases in response to moderate folate depletion in elderly women," American Journal of Clinical Nutrition, 72:998-1003 (2000).

Mass et al., "Arsenic alters cytosine methylation patterns of the promoter of the tumor suppressor gene p53 in human lung cells: a model for a mechanism of carcinogenesis," Mutation Research, 386(3):263-77 (1997).
Gonzalgo et al., Rapid Quantification of methylation differences at specific sites using methylation-sensitive single nucleotide primer extension (Ms-SNuPE), Nucleic Acids Research, 25(12):2529-31 (1997).
Christman et al., "Hypomethylation of DNA during differentiation of Friend erythroleukemia cells," J. Cell Biol., 86:366-70 (1980).
Galm et al., "Enzymatic Regional Methylation Assay: A Novel Method to Quantify Regional CpG Methylation Density," Genome Research (Dec. 14, 2001) (Article published on-line before print in Dec. 2001 at http://www.genome.org/cgi/doi/10.1101/gr.202501).
BIOSIS Biosciences Information Service Abstract, Database Accession No. PREV199800498186 for Fowler et al., "Hypomethylation in cervical tissue: Is there a correlation with folate status?" Cancer Epidemiology Biomarkers & Prevention, 7:901-6 (1998).
BIOSIS Biosciences Information Service Abstract, Database Accession No. PREV199497464668 for Kim et al., "Global DNA hypomethylation increases progressively in cervical dysplasia and carcinoma," Cancer, 74(3):893-9 (1994).
BIOSIS Biosciences Information Service Abstract, Database Accession No. PREV199699249096 for Cravo et al., "Global DNA hypomethylation occurs in the early stages of intestinal type gastric carcinoma," Gut, 39(3):434-8 (1996).
BIOSIS Biosciences Information Service Abstract, Database Accession No. PREV199799315381 for Gloria et al., "DNA hypomethylation and proliferative activity are increased in the rectal mucosa of patients with long-standing ulcerative colitis," Cancer, 78(11):2300-6 (1996).
BIOSIS Biosciences Information Service Abstract, Database Accession No. PREV199800498186 for Fowler et al., "Hypomethylation in cervical tissue: Is there a correlation with folate status?" Cancer Epidemiology Biomarkers & Prevention, 7:901-6 (1998), Abstract only.
BIOSIS Biosciences Information Service Abstract, Database Accession No. PREV199497464668 for Kim et al., "Global DNA hypomethylation increases progressively in cervical dysplasia and carcinoma," Cancer, 74(3):893-9 (1994), Abstract only.
BIOSIS Biosciences Information Service Abstract, Database Accession No. PREV199699249096 for Cravo et al., "Global DNA hypomethylation occurs in the early stages of intestinal type gastric carcinoma," Gut, 39(3):434-8 (1996), Abstract only.
BIOSIS Biosciences Information Service Abstract, Database Accession No. PREV199799315381 for Gloria et al., "DNA hypomethylation and proliferative activity are increased in the rectal mucosa of patients with long-standing ulcerative colitis," Cancer, 78(11):2300-6 (1996), Abstract only.

* cited by examiner

*Primary Examiner*—Christopher M. Babic
(74) *Attorney, Agent, or Firm*—Kriegsman & Kriegsman

(57) ABSTRACT

The invention relates to a method for detecting the methylation status in DNA samples. According to the invention, a DNA methyl transferase and a labeled S-adenosylmethionine derivative allow a detectable label to be covalently bonded to the DNA, in accordance with the respective methylation status of the DNA sample.

9 Claims, No Drawings

SEQUENCE LISTING

<160> NUMBER OF SEQ ID NOS: 2

<210> SEQ ID NO 1
<211> LENGTH: 22
<212> TYPE: DNA
<213> ORGANISM: Homo sapiens

```
-continued

<220> FEATURE:
<221> NAME/KEY: gene
<222> LOCATION: (1)..(22)
<223> OTHER INFORMATION: primer oligonucleotide of gene DAXX

<400> SEQUENCE: 1
taggaaaagg agttggattt tt                                              22

<210> SEQ ID NO 2
<211> LENGTH: 22
<212> TYPE: DNA
<213> ORGANISM: Homo sapiens
<220> FEATURE:
<221> NAME/KEY: gene
<222> LOCATION: (1)..(22)
<223> OTHER INFORMATION: primer oligonucleotide of gene DAXX

<400> SEQUENCE: 2 cccctacct aacctataat ca                                               22
```

METHOD FOR DETECTING DNA METHYLATION USING LABELLED S-ADENOSYLMETHIONINE ANALOGS

The present application is a continuation of U.S. patent application Ser. No. 10/491,847, filed Oct. 13, 2004 now abandoned, which in turn is a national entry under 35 U.S.C. 371 of PCT Application No. PCT/DE02/03844 filed Oct. 4, 2002, both of which are incorporated herein by reference.

The present invention concerns a method for the detection of DNA methylation, particularly of cytosine and adenine, in DNA samples.

The levels of observation that have been well studied in molecular biology according to developments in methods in recent years include the genes themselves, the transcription of these genes into RNA and the translation to proteins therefrom. During the course of development of an individual, which gene is turned on and how the activation and inhibition of certain genes in certain cells and tissues are controlled can be correlated with the extent and nature of the methylation of the genes or of the genome. In this regard, pathogenic states are also expressed by a modified methylation pattern of individual genes or of the genome.

5-Methylcytosine is the most frequent covalently modified base in the DNA of eukaryotic cells. For example, it plays a role in the regulation of transcription, in genetic imprinting and in tumorigenesis. The identification of 5-methylcytosine as a component of genetic information is thus of considerable interest.

5-Methylcytosine positions, however, cannot be identified by sequencing, since 5-methylcytosine has the same base-pairing behavior as cytosine. In addition, in the case of a PCR amplification, the epigenetic information which is borne by the 5-methylcytosines is completely lost.

A relatively new method that in the meantime has become the most widely used method for investigating DNA for 5-methylcytosine is based on the specific reaction of bisulfite with cytosine, which, after subsequent alkaline hydrolysis, is converted to uracil, which corresponds in its base-pairing behavior to thymidine. In contrast, 5-methylcytosine is not modified under these conditions. Thus, the original DNA is converted so that methylcytosine, which originally cannot be distinguished from cytosine by its hybridization behavior, can now be detected by "standard" molecular biology techniques as the only remaining cytosine, for example, by amplification and hybridization or sequencing. All of these techniques are based on base pairing, which is now fully utilized. The prior art which concerns sensitivity is defined by a method that incorporates the DNA to be investigated in an agarose matrix, so that the diffusion and renaturation of the DNA is prevented (bisulfite reacts only on single-stranded DNA) and all precipitation and purification steps are replaced by rapid dialysis (Olek A, Oswald J, Walter J. A modified and improved method for bisulphite based cytosine methylation analysis. Nucleic Acids Res. 1996 Dec. 15; 24(24):5064-6). Individual cells can be investigated by this method, which illustrates the potential of the method. Of course, up until now, only individual regions of up to approximately 3000 base pairs long have been investigated; a global investigation of cells for thousands of possible methylation analyses is not possible. Of course, this method also cannot reliably analyze very small fragments of small quantities of sample. These are lost despite the protection from diffusion through the matrix.

An overview of other known possibilities for detecting 5-methylcytosines can be derived from the following review article: Rein T, DePamphilis M L, Zorbas H. Identifying 5-methylcytosine and related modifications in DNA genomes. Nucleic Acids Res. 1998 May 15; 26(10):2255-64.

The bisulfite technique has been previously applied only in research, with a few exceptions (e.g., Zeschnigk M, Lich C, Buiting K, Dörfler W, Horsthemke B. A single-tube PCR test for the diagnosis of Angelman and Prader-Willi syndrome based an allelic methylation differences at the SNRPN locus. Eur J Hum Genet. 1997 March-April;5(2):94-8). However, short, specific segments of a known gene have always been amplified after a bisulfite treatment and either completely sequenced (Olek A, Walter J. The pre-implantation ontogeny of the H19 methylation imprint. Nat. Genet. 1997 November; 17(3):275-6) or individual cytosine positions have been detected by a "primer extension reaction" (Gonzalgo M L, Jones P A. Rapid quantitation of methylation differences at specific sites using methylation-sensitive single nucleotide primer extension (Ms-SNuPE). Nucleic Acids Res. 1997 Jun. 15; 25(12):2529-31, WO-Patent 95-00669) or an enzyme cleavage (Xiong Z, Laird P W. COBRA: a sensitive and quantitative DNA methylation assay Nucleic Acids Res. 1997 Jun. 15; 25(12):2532-4). Detection by hybridization has also been described (Olek et al., WO 99/28498).

Urea improves the efficiency of bisulfite treatment prior to sequencing of 5-methylcytosine in genomic DNA (Paulin R, Grigg G W, Davey M W, Piper M. Urea improves efficiency of bisulphite-mediated sequencing of 5'-methylcytosine in genomic DNA. Nucleic Acids Res. 1998 Nov. 1; 26(21): 5009-10).

Other publications which are concerned with the application of the bisulfite technique for the detection of methylation in the case of individual genes are: Grigg G, Clark S. Sequencing 5-methylcytosine residues in genomic DNA. Bioessays. 1994 June; 16(6):431-6, 431; Zeschnigk M, Schmitz B, Dittrich B, Buiting K, Horsthemke B, Dörfler W. Imprinted segments in the human genome: different DNA methylation patterns in the Prader-Willi/Angelman syndrome region as determined by the genomic sequencing method. Hum Mol. Genet. 1997 March; 6(3):387-95; Feil R, Charlton J, Bird A P, Walter J, Reik W. Methylation analysis on individual chromosomes: improved protocol for bisulphite genomic sequencing. Nucleic Acids Res. 1994 Feb. 25; 22(4):695-6; Martin V, Ribieras S, Song-Wang X, R10 MC, Dante R. Genomic sequencing indicates a correlation between DNA hypomethylation in the 5' region of the pS2 gene and in its expression in human breast cancer cell lines. Gene. 1995 May 19; 157(1-2):261-4; WO 97-46705, WO 95-15373 and WO-45560.

Another known method is the so-called methylation-sensitive PCR (Herman J G, Graff J R, Myohanen S, Nelkin B D, Baylin S B (1996), Methylation-specific PCR a novel PCR assay for methylation status of CpG islands. Proc Natl Acad Sci USA. September 3; 93(18):9821-6). For this method, primers are used which hybridize either only to a sequence that forms by the bisulfite treatment of a DNA which is unmethylated at the respective position, or, vice versa, primers which bind only to a nucleic acid which forms by the bisulfite treatment of a DNA methylated at the respective position. Amplificates can be produced accordingly with these primers, the detection of which in turn supplies indications of the presence of a methylated or unmethylated position in the sample to which the primers bind.

A newer method is also the detection of cytosine methylation by means of a Taqman PCR, which has become known as Methyl Light (WO 00/70090). It is possible with this method to detect the methylation status of individual positions or a few positions directly in the course of the PCR, so that a subsequent analysis of the products becomes superfluous.

An overview of the prior art in oligomer array production can be derived also from a special issue of Nature Genetics which appeared in January 1999 (Nature Genetics Supplement, Volume 21, January 1999), the literature cited therein and U.S. Pat. No. 5,994,065 on methods for the production of solid supports for target molecules such as oligonucleotides with reduced nonspecific background signal.

Probes with multiple fluorescent labels are used for scanning an immobilized DNA array. Particularly suitable for fluorescent labels is the simple introduction of Cy3 and Cy5 dyes at the 5'-OH of the respective probe. The fluorescence of the hybridized probes is detected, for example, by means of a confocal microscope. The dyes Cy3 and Cy5, among many others, are commercially available.

Matrix-assisted laser desorption/ionization mass spectrometry (MALDI-TOF) is a very powerful development for the analysis of biomolecules (Karas M, Hillenkamp F. Laser desorption ionization of proteins with molecular masses exceeding 10,000 daltons. Anal Chem. 1988 Oct. 15; 60(20): 2299-301). An analyte is embedded in a light-absorbing matrix. The matrix is vaporized by a short laser pulse and the analyte molecule is transported unfragmented into the gaseous phase. The analyte is ionized by collisions with matrix molecules. An applied voltage accelerates the ions in a field-free flight tube. Ions are accelerated to varying degrees based on their different masses. Smaller ions reach the detector sooner than large ions.

MALDI-TOF spectroscopy is excellently suitable for the analysis of peptides and proteins. The analysis of nucleic acids is somewhat more difficult (Gut, I. G. and Beck, S. (1995), DNA and Matrix Assisted Laser Desorption Ionization Mass Spectrometry. Molecular Biology: Current Innovations and Future Trends 1: 147-157.) For nucleic acids, the sensitivity is approximately 100 times poorer than for peptides and decreases overproportionally with increasing fragment size. For nucleic acids, which have a backbone with a multiple negative charge, the ionization process through the matrix is basically inefficient. In MALDI-TOF spectroscopy, the choice of matrix plays an imminently important role. Several very powerful matrices, which produce a very fine crystallization, have been found for the desorption of peptides. In the meantime, several effective matrices have been developed for DNA, but the difference in sensitivity has not been reduced thereby. The difference in sensitivity can be reduced by modifying the DNA chemically in such a way that it resembles a peptide.

Phosphorothioate nucleic acids, in which the usual phosphates of the backbone are substituted by thiophosphates, can be converted by simple alkylation chemistry into a charge-neutral DNA (Gut, I. G. and Beck, S. (1995), A procedure for selective DNA alkylation and detection by mass spectrometry. Nucleic Acids Res. 23: 1367-1373). The coupling of a "charge tag" to this modified DNA results in an increase in sensitivity by the same amount as is found for peptides. Another advantage of "charge tagging" is the increased stability of the analysis in the presence of impurities, which make the detection of unmodified substrates very difficult.

Genomic DNA is obtained from DNA of cells, tissue or other assay samples by standard methods. This standard methodology is found in references such as Fritsch and Maniatis, Molecular Cloning: A Laboratory Manual, 1989.

After the invention of PCR, numerous variants became known in the following few years, which refine this technique for the amplification of DNA. In particular, multiplexing of the PCR (multiplex PCR) should be mentioned here, in which more than 2 specific primers are used, and thus a plurality of different, specific amplifications can be produced in one reaction vessel. Particularly interesting also is the so-called nested PCR, which is used, among other things for the detection of particularly small DNA quantities. This type of PCR is comprised of two successive amplifications, wherein the primers of the second amplification lie within the first amplifiate and are not identical to the primers of the first amplification. In this way, a particular specificity is achieved, since the primers of the second amplification only function if the intended fragment was produced in the first amplification. In contrast, the propagation of possible byproducts of the first amplification in the second amplification is excluded as much as possible.

Accordingly, a great many methods for methylation analysis are prior art. The present invention, however, will provide a possibility for the analysis of the degree of methylation in a genomic DNA segment. It is preferably not necessary to conduct a polymerase reaction, which facilitates conducting the method. It is essential within the framework of a methylation analysis in the field of clinical diagnosis that results of investigation can be made available as rapidly as possible and that the experimental expenditure is kept as low as possible. The method described here is particularly suitable for this purpose.

The method described here for the detection of cytosine methylation is comprised of the combination of the following steps:

First, the genomic DNA sample is selectively treated with a restriction enzyme, so that it is broken up into smaller fragments, preferably on the order of magnitude between 2 kb and 80 kb. The DNA sample is then treated with a bisulfite and a radical trap, which will prevent the decomposition of the DNA, and the bisulfite adducts that are formed are hydrolyzed under alkaline conditions. In this way, all methylated cytosines remain essentially unchanged, while unmethylated cytosine bases are converted to uracil.

Now, by using a methyltransferase in the next step, it can be determined as to how far this reaction has occurred at given positions. It is thus possible with the methyltransferase Sssl, which selectively methylates the sequence 5'-CpG-3' with the use of a modified S-adenosylmethionine derivative to distinguish whether a cytosine is now found at this position, just as previously, or whether it has been converted into uracil, since only the methylated positions can be fluorescently labeled by the modified S-adenosylmethionine derivative and, for example, Sssl. Other enzymes are more sequence-specific than Sssl and thus additional conclusions can be drawn relative to the sequence context. Since these positions, however, must also still be methylated after the bisulfite treatment, a demethylation must be conducted first. This is preferably achieved by means of a copying reaction or a PCR. This also has the advantage that one knows precisely which segments of the genomic DNA sample will be subsequently investigated for methylation.

The above-mentioned modified S-adenosylmethionine derivative has the property that S-adenosylmethionine which functions as a methyl group donor in enzymatic DNA methylation must be substituted such that the methyl group is replaced by a corresponding fluorescently labeled analog. Instead of a methyl group, The methyltransferase thus transfers a corresponding fluorescently labeled analog.

The modified S-adenosylmethionine derivatives that can be employed according to the invention can be produced in a way known in and of itself. Derivatives of this type are produced, in which the fluorophore is known in and of itself. Molecules yielding suitable fluorescence are familiar to the person skilled in the art. These molecules emitting fluorescence are then coupled with S-adenosylmethionine in a suitable way. This is particularly accomplished in such a way that compounds are formed which simultaneously transfer the groups emitting fluorescence when the methyl groups are transferred.

After a PCR, the amplificates are thus fluorescently labeled in a sequence-specific manner with the modified S-adenosylmethionine derivative and a methyltransferase, and this will happen only when a methylation has been present previously at the respective positions in the genomic DNA sample. Now if a fragment analysis is conducted with conventional methods such as (capillary) gel electrophoresis, chromatography or similar methods, then only those fragments that were previously methylated at the position under investigation will have a fluorescent label.

In a particularly preferred variant of the method, several fragments and more preferably several positions in these fragments will be simultaneously investigated for methylation in this way. This can be done by successively labeling the modified S-adenosylmethionine derivative with different dyes in combination with different sequence-specific methyltransferases.

It is also possible to work with several pairs of primers simultaneously in the PCR and thus to conduct a multiplex PCR. If the amplificates generated in this way have different lengths, then a simultaneous analysis by means of one of the above-named methods is possible.

Another possibility of the DNA methylation analysis consists of the use of the modified S-adenosylmethionine derivative together with a methyltransferase such as Dnmt1, which is specific for hemimethylated double strands and belongs to the so-called maintenance methyltransferases. In this method, one takes advantage of the fact that after a copying reaction of a specific segment of the genomic DNA sample, the same segment is present hemimethylated at the positions which were present methylated in the genomic DNA, while the positions which are again present unmethylated are those which were also present unmethylated prior to the copying reaction. The modified S-adenosylmethionine derivative in combination with Dnmt1 will selectively incorporate a fluorescent label only at the positions that were previously methylated.

This [label] can now be made visible by means of different methods. The lack of exponential amplification, which would make the use of Dnmt1 impossible in this sense, is the limiting factor for this variant.

Dnmt1 can generally be utilized, however, also in combination with the modified S-adenosylmethionine derivative for the detection of unmethylated positions in a pool of DNA samples. With this procedure, heteroduplexes are formed from the double-stranded DNA sample molecules after a melting and reannealing step. Hemimethylated double strands which can be selectively fluorescently labeled by Dnmt1 and modified S-adenosylmethionine derivatives are formed after the reannealing at those positions at which methylation was partially present. This method can be used, on the one hand, for finding differentially methylated CpG positions. On the other hand, however, by adding unmethylated DNA, preferably a fluorescence labeling can be produced, if methylated positions were present in a sample. Also on the other hand, a fluorescence labeling of unmethylated DNA is selectively possible, if a mixing in of a DNA methylated sample is carried out beforehand.

The methylated and unmethylated standard DNA samples necessary for the foregoing experiments are preferably generated by methylating a genomic DNA sample with Sssl. For unmethylated DNA, DNA which has been isolated from peripheral blood is preferably used, which is present unmethylated at most of the positions under investigation. Alternatively, for example, DNA isolated from sperm can be used.

The fluorescently labeled genomic DNA can be analyzed as described above. An additional interesting possibility consists of conducting a 2D gel electrophoresis, with which information can now additionally be obtained for any fragment with respect to its methylation status.

Another variant of the method consists of the fact that modified S-adenosylmethionine derivatives are used for transferring ideally fluorescing groups, which inhibit a subsequent polymerase reaction at the DNA template modified in this way. At those positions at which such a group was incorporated, the polymerase reaction is preferably interrupted. This could be utilized for conducting a sequencing reaction, comparable to a Sanger sequencing, wherein, however, in this variant, not specific base sequences, but rather positions that can be methylated under the respectively selected conditions would be indicated. The positions that can be methylated each time are determined, first of all, according to the methylation status of the template that is present and, secondly, according to the sequence specificity of the methyltransferase used.

The following example explains the invention.

EXAMPLE

A genomic DNA sample was digested with the restriction enzyme Mssl.

A sodium bisulfite solution was used for the bisulfite reaction. The desulfonation was carried out with 50 μl of a 50 mM Tris-HCl solution at pH 9 for 20 minutes at 96° C. The DNA treated with bisulfite was amplified with the primer oligonucleotides TAGGAAAAGGAGTTGGATTTTT (SEQ ID NO: 1) and CCCCCTACCTAACCTATAATCA (SEQ ID NO: 2) of the gene DAXX.

The amplification was conducted as follows: 95° C.-15 min, 40 cycles: 94° C.-1:00 min, 55° C.-0:45 min, 72° C.-1:30 min and a final elongation at 72° C.-10 min.

In a subsequent reaction, fluorescently labeled S-adenosylmethionine derivative, which was produced with analogous methods in a way known in and of itself was used as the methyl group donor for the methylase Sssl (NEB) For this, 500 ng of DNA were incubated according to the manufacturer's instructions for 8 hours at 37° C. with the use of 0.5 unit of Sssl as well as the S-adenosylmethionine derivative and the reaction buffer belonging thereto.

The cytosines labeled by the fluorescently labeled S-adenosylmethionine derivatives were detected in a fragment analysis.

The invention claimed is:

1. A method for DNA methylation analysis of a genomic DNA sample, said method comprising the steps of:
    a) converting a genomic DNA sample by a copying reaction so that methylated positions in the genomic DNA sample become hemimethylated whereas unmethylated positions in the genomic DNA sample remain unmethylated;
    b) then, treating the genomic DNA sample with at least one labeled S-adenosylmethionine derivate and a methyltransferase specific for hemimethylated double-stranded DNA, whereby the at least one labeled S-adenosylmethionine derivate becomes incorporated into the genomic DNA sample at previously methylated positions; and
    c) then, detecting the presence of the at least one labeled S-adenosylmethionine derivate.

2. The method as claimed in claim 1 wherein the methyltransferase is Dnmt1.

3. The method as claimed in claim 1 wherein said detecting step comprises using at least one of gel electrophoresis, capillary gel electrophoresis, 2D gel electrophoresis, and chromatography.

4. A method for the analysis of cytosine methylation in a pool of DNA samples, said method comprising the steps of:
    a) generating hemimethylated double strands by means of melting and re-annealing the DNA samples;
    b) labeling unmethylated positions within the hemimethylated double strands using Dnmt1 and at least one labeled S-adenosylmethionine derivate; and
    c) then, detecting the presence of the at least one labeled S-adenosylmethionine derivate within the hemimethylated double strands.

5. The method as claimed in claim 4 further comprising, prior to said generating step, the step of adding unmethylated DNA to the DNA samples.

6. The method as claimed in claim 4 further comprising, prior to said generating step, the step of adding completely methylated DNA to the DNA samples.

7. The method as claimed in claim 4 wherein said detecting step comprises using at least one of gel electrophoresis, capillary gel electrophoresis, 2D gel electrophoresis, and chromatography.

8. The method as claimed in claim 4 wherein said at least one labeled S-adenosylmethionine derivate inhibits a subsequent polymerase reaction on the DNA template.

9. The method as claimed in claim 8 further comprising a subsequent sequencing reaction.

\* \* \* \* \*